United States Patent [19]

Allen et al.

[10] Patent No.: US 6,383,792 B1
[45] Date of Patent: May 7, 2002

[54] RAQ GENES AND THEIR USES

[75] Inventors: Maxine J. Allen, Encinitas; Marc Rutter, San Diego; Alan J. Buckler, Cardiff, all of CA (US)

[73] Assignee: AxyS Pharmaceuticals, Inc., South San Francisco, CA (US)

[ * ] Notice: Subject to any disclaimer, the term of this patent is extended or adjusted under 35 U.S.C. 154(b) by 0 days.

[21] Appl. No.: 09/454,818

[22] Filed: Dec. 3, 1999

Related U.S. Application Data

[62] Division of application No. 09/078,317, filed on May 13, 1998, now Pat. No. 6,017,710.

[51] Int. Cl.[7] .............................. C12N 9/14; C07K 1/00
[52] U.S. Cl. ....................................... 435/195; 530/350
[58] Field of Search ............................... 435/69.1, 195; 530/350; 536/23.2

[56] References Cited

U.S. PATENT DOCUMENTS 5,973,130 A * 10/1999 Hillman et al. ............. 536/23.1

OTHER PUBLICATIONS

Bos, J.L., "ras Oncogenes in Human Cancer: A Review," *Cancer Res.* 49:4682–4689 (Sep. 1, 1989).
Hatta, et al., "Ovarian Cancer Has Frequent Loss of Heterozygosity at Chromosome 12p12.3–13.1 (Region of TEL and Kip 1 loci) and Chromosome 12q23–ter: Evidence for two New Tumour Suppressor Genes," *British Journal of Cancer* 75(9):1256–1262 (1997).
Johansson, et al., "Cytogenetic Deletion Maps of Hematologic Neoplasms: Circumstantial Evidence for Tumor Suppressor Loci," *Genes, Chromosomes & Cancer* 8(4):205–218 (Dec. 1993).
Manenti, et al., "Association of Chromosome 12p Genetic Polymorphisms with Lung Adenocarcinoma Risk and Prognosis," *Carcinogenesis* 18(10):1917–1920 (Oct. 1997).
Symons, Marc, "The Rac and Rho Pathways as a Source of Drug Targets for Ras–Mediated Malignancies," *Current Opinion in Biotechnology* 6:668–674 (1995).
Zachos, et al. "Expression of ras Proto–Oncogenes: Regulation and Implications in the Development of Human Tumors," *Crit. Rev. Oncol. Hematol.* 26(2):67–75 (1997).

Genbank accession No. AA031734 (May 9, 1997).
Genbank accession No. AA131239 (May 14, 1997).
Genbank accession No. AA437054 (May 30, 1997).
Genbank accession No. AA663946 (Nov. 12, 1997).
Genbank accession No. AA769749 (Feb. 8, 1998).
Genbank accession No. AA782027 (Feb. 5, 1998).
Genbank accession No. N98847 (Apr. 10, 1996).
Genbank accession No. D62865 (May 21, 1996).
Genbank accession No. AA742672 (Jan. 22, 1998).
Genbank accession No. H01201 (Jun. 19, 1995).
Genbank accession No. R40247 (May 22, 1995).
Genbank accession No. D62925 (May 21, 1996).
Genbank accession No. H01299 (Jun. 19, 1995).
Genbank accession No. D79833 (Dec. 15, 1995).
Genbank accession No. Z19345 (Sep. 21, 1995).
Genbank accession No. AA037415 (May 10, 1997).
Genbank accession No. D79915 (Dec. 15, 1995).
Genbank accession No. AA663274 (Nov. 12, 1997).
Genbank accession No. F00427 (Sep. 21, 1995).
Genbank accession No. AA564698 (Sep. 5, 1997).
Genbank accession No. R14297 (Apr. 12, 1997).
Genbank accession No. AA214398 (Mar. 12, 1998).
Genbank accession No. R55855 (May 23, 1995).
Genbank accession No. AA131358 (May 14, 1997).
Genbank accession No. M31468 (Jun. 15, 1990).
Genbank accession No. Y07565 (Dec. 2, 1996).
Genbank accession No. U71203 (Feb. 7, 1997).
Genbank accession No. X15014 (Sep. 12, 1993).
Genbank accession No. X08004 (Jul. 6, 1989).
Genbank accession No. Z14134 (Mar. 31, 1995).
Genbank accession No. J04160 (Sep. 15, (1989).

* cited by examiner

*Primary Examiner*—Rebecca E. Prouty
*Assistant Examiner*—M. Monshipouri
(74) *Attorney, Agent, or Firm*—Paula A. Borden; Pamela J. Sherwood Bozicevic, Field & Francis, LLP

(57) ABSTRACT

The invention features polynucleotides encoding novel GTP-binding polypeptides, hereinafter referred to as RAQ polypeptides; expression vectors comprising a RAQ polynucleotide of the invention; isolated cells comprising a RAQ-encoding vector; a transgenic non-human animal comprising an alteration in a RAQ gene; and the use of RAQ polynucleotides in detecting in an individual the presence of a genetic polymorphism of a RAQ gene. The invention further features novel RAQ polypeptides; monoclonal antibodies specific for RAQ polypeptides; and a method for making RAQ polypeptides.

1 Claim, 3 Drawing Sheets

Figure 1A

```
   1  TCACTATAGG GCTCGAGCGG CCGCCCGGGT AGGTCCGCAG TCCCTCCGCC
  51  GCTAGTCGGA GCGAGCGCGA GTGAGGAGAC CCCCGCCGGG CCACTGGCAC
 101  TTGCTTCTGC GGCGAGTCCC ACCCACGACC GCAGCCCAGC AACTCGCAAA
 151  CGCAACCTGA AGCCTGGGCT GCGCAGTGTG GGAGGGCTTC GCGATCTTGG
 201  GGGACCCATT CCGAACTTGC AGAGGACCGT AGCTCTCCTG GCCTGGAGAG
 251  TGTGAACAGG ATTGTGGACT CTTCCAAGAT TCACAATGAT ATGGTGAATC
 301  CAAAGACTGG AACCAAAAAG ATTTACTCAG TGCTTTAGTT TTAACAACAG
 351  TAAATTGTCT ACCAACACCC ATCATGGCTA AAAGTGCGGA GGTCAAACTG
 401  GCAATATTTG GGAGAGCAGG CGTGGGCAAG TCAGCTCTTG TAGTGAGATT
 451  TCTGACCAAA CGGTTCATCT GGGAATATGA TCCCACCCTC GAATCAACCT
 501  ACCGACACCA AGCAACCATC GATGATGAAG TTGTTTCCAT GGAGATACTA
 551  GACACTGCTG GTCAGGAAGA TACCATTCAG AGGGAGGGGC ACATGCGATG
 601  GGGGGAAGGC TTTGTGCTGG TCTACGACAT TACTGACCGA GGAAGTTTTG
 651  AGGAAGTGCT GCCACTTAAG AACATCCTAG ATGAGATCAA AAAGCCCAAG
 701  AATGTGACTC TCATCTTGGT TGGAAACAAA GCTGACTTGG ACCACTCCAG
 751  GCAGGTTAGC ACAGAAGAAG GAGAGAAGCT GGCCACAGAA TTGGCTTGTG
 801  CTTTTTACGA GTGCTCTGCC TGCACTGGAG AAGGGAATAT CACAGAGATA
 851  TTCTATGAAT TGTGTCGAGA GGTGCGTCGC CGGAGGATGG TGCAGGGCAA
 901  GACGAGGCGA CGCAGCTCCA CCACGCATGT CAAGCAAGCC ATTAACAAGA
 951  TGCTCACCAA AATCAGTAGT TAGGCAGCCC AGCTGAGGTG GACCAACTAA
1001  TTGGAAACAC TCTTCCCCTT CTGTTCCCCT TTCAAAAATA AAACAAAATA
1051  TTGCATTCTT TGTTTGGATT CTGAGAAATG TCTGGGCTTC CCATTGTTTC
1101  TGGCCTCTAA TAGGTTGGGA AGTTTAGCG TGTTTTATGC AATTTCAGTG
1151  CTAACAATTT CTTCCTTTCC TGCTTGAATA AGATACACTC TAATGGCATT
1201  TGAACATGTA ATCACCAGAG ATTCTGAAAT GACTGGTTTA TGTTAAGCTA
1251  TTTTTAGGCA TCTTCACCTT GCTTTAAGTA GGTTGAAGTT TTTGCAAAGG
1301  CATTTAAAAA TTCAATTTCT TGTCAGATAC TACAAATAAT TTTCTTAAAA
1351  GTCTAAGATA GCAGAAAATA CAGTAAAAAC ACAGGAGAAG AAGCTGAGCT
1401  ATTGGAACAG GAAATAGAAG GAACTCTAGT TTCTGTTTGA AGTGAGGATT
1451  TTCTGAATTA TCTAATATCA TCTAGGTTTT CTTTAAAATT TTATTTTGTT
1501  CTTCAGTTCA AGCATCTTCT CACTAATGTT TTTCACTATA ACAGAGAATT
1551  CATTTCAATT TGAGTTGGTT CTCTCAATGA TCTATTGATC ATTACACCCT
1601  AACTCTCCTT CCTTGGCTCA ACAATATTT TCCCTATAAC AAAGGCAATA
1651  GGACACAAAA TTCACATCCT GCTGGGCCTT TTTTCATCAA GTCAGGGTGA
1701  TATAAAAACA TTGGAAGTCT TTTCACCAAA CCCTGACTTT ATTGAATGCT
1751  AGTAGAAGAT GTAGAATTAG AGACATCTGA TTTGTTTATC ACCTTAGCAG
1801  AAAAACCACA GTCCAAAAGA CAAGCAAATT AAGAATGGAG CTTAACCATG
1851  CCTCCATTGG GAAGTCTAGA CTTTGAGCCA GGTACAGTAA GAAAAATTAG
1901  CCTCTGATTC ATTAAGTTTG CCACATGACT TATTTTGATA TTTTGGATAC
1951  ATTAACTCAC TTAGGAGAAT TCAGAAAAGA ATGGGTGATT AAAGTTCATT
2001  ACAGCTGAAT AAATGTGTCT AAAACAGACT CTTGTATTCT GAAAGTACAG
2051  TCTACAACTG ATAAAACCTT ATGATTCTTT CTCCCCCAT TATGCCCCTA
2101  TATATATCAA GATTTGGGTA CTTTATTTTA GTAGAAAATA TATATCTTTT
2151  ACATATGTAT GTATTTATAA ATGCATAGAT ATATGTATAA AAATTTGTAA
2201  GCGTTAGCGG CATTAATTCA CCAATGCATT TGGACAACTT GATGTAACTG
2251  ACTTTATTTT ATGTGACTAT AATAAAAGC ATAATTTTCT CAAAAAAAAA
2301  AAAAAAAAA
```

Figure 1B

```
  1  MAKSAEVKLA IFGRAGVGKS ALVVRFLTKR FIWEYDPTLE STYRHQATID
 51  DEVVSMEILD TAGQEDTIQR EGHMRWGEGF VLVYDITDRG SFEEVLPLKN
101  ILDEIKKPKN VTLILVGNKA DLDHSRQVST EEGEKLATEL ACAFYECSAC
151  TGEGNITEIF YELCREVRRR RMVQGKTRRR SSTTHVKQAI NKMLTKISS*
```

Figure 2

```
             1                                                              50
huRin        --meveneas  cspgsasggs  reyKvvmlGa  GGVGKSAmTm  QFishqFpdy
huRit        mdsgtrpvgs  cc.sspagls  reyKlvmlGa  GGVGKSAmTm  QFishrFped
ddRasD       ----------  ---------m  teyKlvivGg  GGVGKSAlTi  QliqnhFide
RasS         ----------  ---------m  fnfKlvlvGp  GGVGKSclTi  QFiaqkFvde
huRap1b      ----------  ---------m  reyKlvvlGs  GGVGKSAlTv  QFvqgiFvek
huTC21       -------ma   aagwrdgsgq  ekyrlvvvGg  GGVGKSAlTi  QFiqsyFvtd
huRalA       -------ma   ankpkgqnsl  alhKvimvGs  GGVGKSAlTl  QFmydeFved
Raq          ----------  ------maks  aevKlaifGr  aGVGKSAlvv  rFltkrFiwe
Consensus    ----------  ----------  ---K----G-  GGVGKSA-T-  QF----F---
                                                      I 51                                                             100
huRin        hDPTiEDaYk  tqvriDnepa  yldILDTAGQ  aeftAmReqY  MRgGeGFiic
huRit        hDPTiEDaYk  iririDdepa  nldILDTAGQ  aeftAmRdqY  MRaGeGFiic
ddRasD       yDPTiEDsYr  kqvsiDdetc  lldILDTAGQ  eeysAmRdqY  MRtGqGFlcv
RasS         yDPTlEDsYr  kqttvDgeec  lldIyDTAGQ  edfsAvRdqY  MRtGeGFlcv
huRap1b      yDPTiEDsYr  kqvevDaqqc  mleILDTAGt  eqftAmRdlY  MknGqGFalv
huTC21       yDPTiEDsYt  kqcviDdraa  rldILDTAGQ  eefgAmReqY  MRtGeGFllv
huRalA       yePTkaDsYr  kkvvlDgeev  qidILDTAGQ  edyaAiRdnY  fRsGeGFlcv
Raq          yDPTlEstYr  hqatiDdevv  smeILDTAGQ  ed.tiqRegh  MRwGeGFvlv
Consensus    -DPT-ED-Y-  -----D----  ---ILDTAGQ  ----A-R--Y  MR-G-GF---
                 II                      III 101                                                            150
huRin        ySvTdrqSFq  eaakfkelif  qVrhtyeiPl  vLVGNKiDLe  qfRqVsteEG
huRit        ySiTdrrSFh  evrefkqliy  rVrrtddtPv  vLVGNKsDLk  qlRqVtkeEG
ddRasD       ySiTsrsSyd  eiasfreqil  rVkdkdrvPl  iLVGNKaDLd  heRqVsvnEG
RasS         ySiTylqSFk  eihrlhnhll  kVkdldsvPf  vLVGNKcDLn  eyReVstaEG
huRap1b      ySiTaqstFn  dlqdlreqil  rVkdtddvPm  iLVGNKcDLe  deRvVgkeqG
huTC21       fSvTdrgSFe  eiykfqrqil  rVkdrdefPm  iLiGNKaDLd  hqRqVtqeEG
huRalA       fSiTemeSFa  atadfreqil  rVkedenvPf  lLVGNKsDLe  dkRqVsveEa
Raq          ydiTdrgSFe  evlplknild  eikkpknvtl  iLVGNKaDLd  hsRqVsteEG
Consensus    -S-T---SF-  ----------  -V------P-  -LVGNK-DL-  --R-V---EG
                                                      IV 151                                                            200
huRin        lsLAqey.nc  gffEtSAalr  .fciddaFhg  LvReirkkes  mpsl.mekkl
huRit        laLAref.sc  pffEtSAayr  .yyiddvFha  LvReirrkek  eavlamekks
ddRasD       qeLAkgf.nc  pfmEsSAksr  .inveeaFys  LvReirkelk  gdqssgkaqk
RasS         eeLAkkl.nc  kflEtSAker  .invsesFye  LvRevkkarq  snqhsnsqeq
huRap1b      qnLArqwnnc  aflEsSAksk  .invneiFyd  LvRqinrktp  vpgkrkkssc
huTC21       qqLArql.kv  tymEaSAkir  .mnvdqaFhe  LvRvirkfqe  qecppspept
huRalA       knrAeqw.nv  nyvEtSAktr  .anvdkvFfd  LmReirarkm  edskekngkk
Raq          ekLAtelaca  fy.EcSactg  egniteiFye  LcRevrrrrm  vqgktrrrss
Consensus    --LA------  ---E-SA---  -------F--  L-R-------  ----------
                              V 201         221
huRin        krkdslwkkl  kgslkkkren  mt  (SEQ ID NO:9)
huRit        kpknsvwkrl  kspfrkkkds  vt  (SEQ ID NO:10)
ddRasD       kkkqclil--  ----------  --  (SEQ ID NO:11)
RasS         ntdqpikkkk  scnll-----  --  (SEQ ID NO:12)
huRap1b      qll-------  ----------  --  (SEQ ID NO:13)
huTC21       rkekdkkgch  cvif------  --  (SEQ ID NO:14)
huRalA       krkslakrir  erccil----  --  (SEQ ID NO:15)
Raq          tthvkqaink  mltkiss---  --  (SEQ ID NO:2)
Consensus    ----------  ----------  --  (SEQ ID NO:16)
```

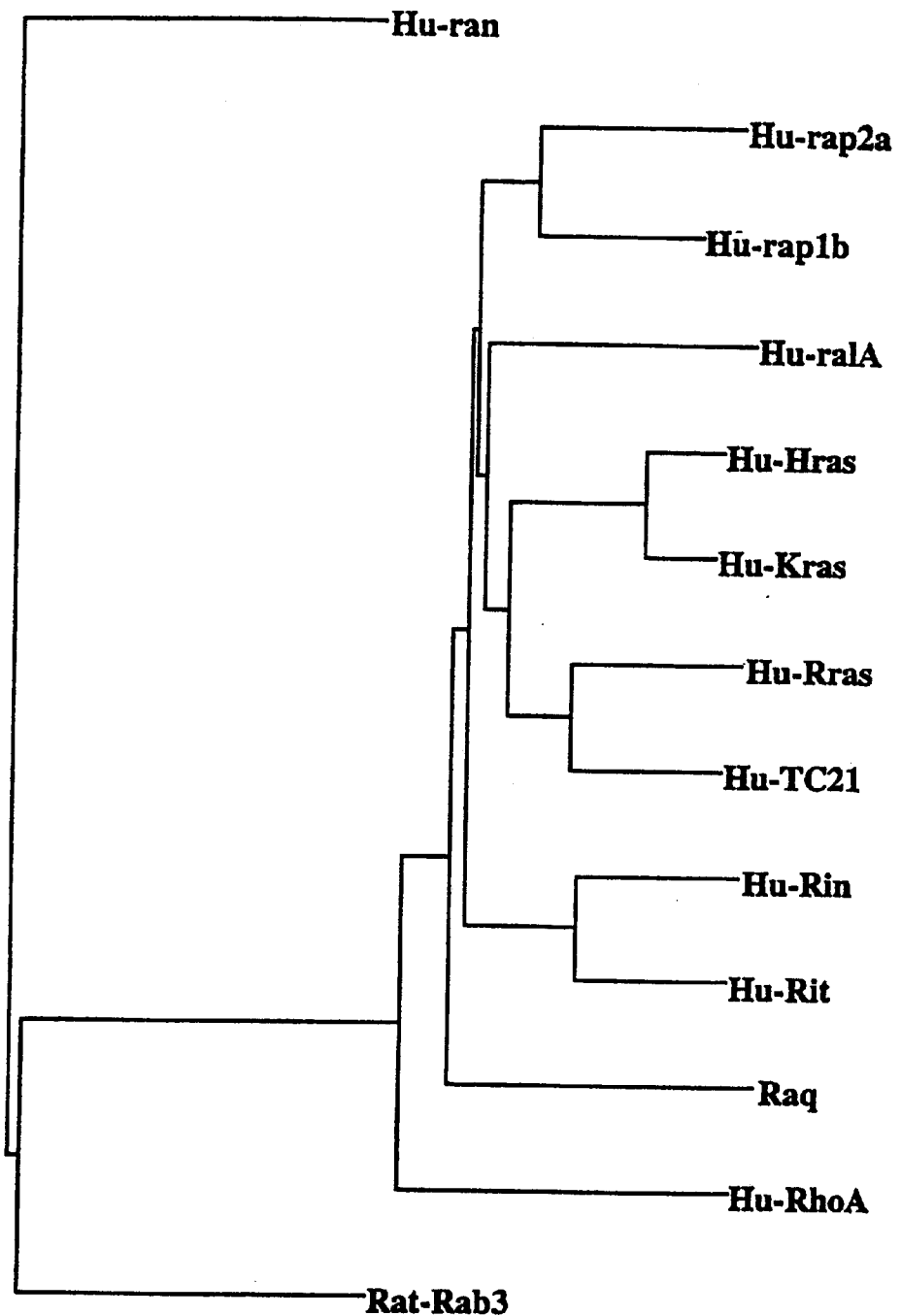
 Divergence scale = 2 aa substitutions.
Figure 3.

RAQ GENES AND THEIR USES

CROSS-REFERENCE

This application is a divisional of U.S. patent application Ser. No. 09/078,317, filed May 13, 1998, now U.S. Pat. No. 6,017,710, issued Jan. 25, 2000.

BACKGROUND OF THE INVENTION

GTP-binding proteins represent a class of small, approximately 20 to 30 kDa, monomeric, receptor-coupled GTPases, which mediate signal transduction in eukaryotic cells. GTP-binding proteins act as molecular switches, alternating between an active GTP-bound state and an inactive GDP-bound state. Subfamily members of the GTP-binding proteins include Ras proteins, associated with the regulation of cell proliferation and differentiation, Rho and Rac proteins, associated with the regulation of cytoskeletal assembly, and Rab, Arf, Sar and Ran proteins, associated with the regulation of vesicular transport (Bourne et al. (1991), Nature. 349:117–127; Hall and Zerial (1995) General introduction. In: "Guidebook to the Small GTPases" (M. Zerial and L. A. Huber Eds.), pp. 3–11, Sambrook and Tooze, Oxford University Press).

The Ras subfamily members share four conserved domains which, as demonstrated through both mutagenic studies and X-ray crystallography, are involved in the binding and hydrolysis of guanine nucleotides. Many Ras proteins also share a fifth conserved carboxy-terminal domain required for posttranslational modification of the Ras proteins prior to membrane localization (Boguski and McCormick (1993) Nature 366:643–654; Hall and Zerial (1995), supra).

At least nine of the sixty or so members of the Ras-related have greater than about 50% amino acid identity to H-, K-, and N-ras oncogenes (Hall and Zerial (1995), supra). These include R-ras1 and its related proteins R-ras-2(TC21) and the recently identified R-ras3 (Hall and Zerial (1995), supra; Kimmelmann et al. (1997), Oncogene 15(22):2675–2685) which share about 55% amino acid identity with H-ras, including an identical effector domain, and are about 70% identical to one another. The Rap proteins (Rap1a and b, Rap2a and b) also share a conserved effector domain and about 50% protein identity with H-ras. The RaIA and RaIB proteins also belong to the ras subfamily, with about 50% peptide identity to H-ras, although there is a one residue difference in their effector domain (Hall and Zerial (1995).

Recently two small GTPases, termed Rin and Rit, were identified. Rin and Rit share about 50% identity and four conserved GTP-binding motifs of Ras proteins,(Lee et al. (1996) J. Neurosci. 16(21):6784–6794). However, these two proteins were unusual in that they lacked the known CAAX recognition signal for C-terminal lipidation found in each of the other Ras subfamily members.

The Ras GTP-binding protein is coupled to a tyrosine kinase receptor. The formation of an agonist-receptor complex facilitates GTP binding to the Ras protein, whereupon the protein bound GTP is hydrolyzed to GDP via the intrinsic GTPase activity of the Ras protein. The GDP dissociates from the Ras protein and it reverts to its inactive form. This cycling between inactive and active states initiates a mitogen-activated kinase cascade which leads to the phosphorylation of a number of transcription factors in the nucleus which culminates in cell proliferation and differentiation.

GTP binding and its hydrolysis to GDP are catalyzed by at least two classes of proteins: guanine nucleotide exchange factors, which promote exchange between bound GDP and cytoplasmic GTP, and GTPase activating proteins, which stimulate the low intrinsic GTP hydrolysis by the GTPases (Boguski and McCormick (1993), Nature. 366, pp 643–654; Feig (1993), Science. 260, pp 767–768). Mutations in the GTP-binding proteins affecting the nucleotide exchange or GTP hydrolysis can stabilize the GTP- or GDP-bound conformation and thereby cause the GTP-binding proteins to be constitutively active or inactive. For example, Ras genes with point mutations are known, wherein the intrinsic GTPase activity of Ras GTP-binding protein is insensitive to GTPase activating proteins.

The link between mutations in Ras genes and cancer is well established. For example, there is a strong association between abnormal signal transduction involving activated Ras genes and the development of a variety of tumors. In fact, mutations in Ras genes are found in 30% of all human tumors and in some the mutation frequency approaches 100%, e.g., pancreatic adenocarcinoma. The number of genes encoding Ras or Ras-related proteins is unknown, but it is clear that their role in cellular processes is of crucial importance. Accordingly, the discovery of novel Ras-related genes will advance the understanding and treatment of human disease.

Relevant Literature

EST sequences present within the RAQ polynucleotide sequence of the invention are summarized in Table 1 below. The nucleotide residues of the RHOH sequence to which there is greater than 90% identity to a provided EST are indicated in the last column.

TABLE 1

Relevant EST sequences.

| Sequence accession no. | Read orientation | Clone ID | Extent RAQ sequence (SEQ ID NO:3) having >90% identity (RAQ nt residue numbers) |
|---|---|---|---|
| AA031734 | 5' | IC470515 | 1793–2277 |
| AA131239 | 3' | IC 503581 | 1776–2308 |
| AA437054 | 5' | IC 758247 | 1364–1811 |
| AA663946 | 3' | IC 855719 | 1887–2292 |
| AA769749 | 3' | IC 1324233 | 1877–2294 |
| AA782027 | 3' | IC 1376649 | 1918–2292 |
| N98847 | 5' | IC 278823 | 1189–1548 |
| D62865 | 5' | GEN-333F03 | 1891–2207 |
| AA742672 | 3' | IC 1257275 | 1980–2292 |
| HO1201 | 3' | IC 150011 | 1964–2284 |
| R40247 | 3' | IC 28777 | 2019–2299 |
| D62925 | 5' | GEN-340E03 | 1764–2069 |
| HO1299 | 5' | IC 150011 | 1364–1616 |
| D79833 | 5' | GEN-334H02 | 1764–2064 |
| Z19345 | 5' | 17C02 | 1021–1315 |
| AA037415 | 3' | IC484600 | 2022–2292 |
| D79915 | 5' | GEN-354F08 | 1764–2027 |
| AA663274 | 3' | IC 853301 | 2007–2255 |
| F00427 | 3' | 17C02 | 2043–2273 |
| AA564698 | 3' | IC993282 | 2158–2291 |
| R 14297 | 5' | IC 28777 | 267–512 |
| AA214398 | 5' | IC649419 | 407–620 |
| R55855 | 5' | IC 40732 | 651–1020 |
| AA131358 | 5' | IC 503581 | 886–1451 |

IC = IMAGE clone

The sequence of human genes related to RAQ may be accessed at Genbank at the indicated accession numbers: R-ras2 (TC21), Genbank:M31468 Genbank:Y07565; Rin (human, Genbank accession #=Y07565); Rit, Genbank:U71203; RaIA, Genbank:X15014; and Rap1b, Genbank:X08004. The sequence of Dictostylium discoideum genes sharing homology with human RAQ may be accessed at Genbank at the indicated accession numbers: RasS, Genbank:Z14134; and RasD, Genbank:J04160.

The role of ras oncogenes in human cancer is reviewed in Zachos et al. (1997) *Crit Rev Oncol Hematol* 26(2):65–75 and in Bos (1989) *Cancer Res.* 49:4682–4689. The targeting of small GTPases for cancer therapies is discussed in Symons (1995) *Curr. Opin. Biotechnol.* 6:668–74.

The association of the 12p12-13 cytoband region with cancer is described in several references. The possibility of a human pulmonary adenoma susceptibility 1 (Pas1) locus homolog at 12p12-13 is discussed in Manenti et al. (1997) *Carcinogenesis* 18(10):1917–1920. Pas1 is a major locus affecting inherited predisposition to lung cancer in mice within the syntenic chromosome region. Johansson et al. ((1993) *Genes, Chromosomes, Cancer.* 8:205–218) and Hatta et al. ((1997) *Br J Cancer.* 75(9):1256–1262, suggested that a new tumor suppressor gene may lie within the 12p12-13 region.

SUMMARY OF THE INVENTION

The invention features polynucleotides encoding novel GTP-binding polypeptides, hereinafter referred to as RAQ polypeptides; expression vectors comprising a RAQ polynucleotide of the invention; isolated cells comprising a RAQ-encoding vector; a transgenic non-human animal comprising an alteration in a RAQ gene; and the use of RAQ polynucleotides in detecting in an individual the presence of a genetic polymorphism of a RAQ gene.

The invention further features novel RAQ polypeptides; monoclonal antibodies specific for RAQ polypeptides; and a method for making RAQ polypeptides.

BRIEF DESCRIPTION OF THE DRAWINGS

FIG. 1A shows the nucleotide sequence (SEQ ID NO:3) of the RAQ protein. The sequence from nucleotide 406 to 2309 is from INAGE clone 649419. The nucleotides 1 to 405 are from 5' RACE clones. Th coding region (SEQ ID NO:01) is in bold. The 5' UTR is 373 nt, the 3' UTR is 1318 nt.

FIG. 1B shows the predicted polypeptide sequence of RAQ (SEQ ID NO:2).

FIG. 2 is a sequence alignment of the RAQ protein with related human small ras GTPases Rin, Rit, TC21, Rap1b, RaIA, and *Dictostylium discoideum* small ras GTPases RasS and RasD. Dots represent spaces to optimize alignment. Residues occurring in 7 or more of these proteins are capitalized and comprise the consensus sequence. The five conserved domains characteristic of small GTP-binding proteins are underlined; I, III, IV and V are GTP-binding domains, II is the effector loop.

FIG. 3 is a dendrogram showing the phylogenetic relationship between RAQ and other small GTPase proteins selected from the ras-subfamily.

DESCRIPTION OF THE SPECIFIC EMBODIMENTS

Definitions

Unless otherwise stated, the following terms used in the specification and claims are defined for the purposes of this application and have the meanings given below:

As used herein, the term "RAQ gene" is intended to generically refer to both the wild-type and allelic forms of the sequence, unless specifically denoted otherwise. As it is commonly used in the art, the term "gene" is intended to refer to the genomic region encompassing 5' UTR, exons, introns, and 3' UTR. Of the 5' UTR and 3'UTR, those sequences involved in the regulation of expression are of particular interest; such sequences are positioned generally up to about 20 kb beyond the coding region, but possible further in either the 5' or 3' direction. Individual segments may be specifically referred to, e.g. exon 1, intron 2, etc. Combinations of such segments that provide for a complete RAQ polypeptide may be referred to generically as a protein coding sequence, or may specifically refer to the intended RAQ polypeptide.

"RAQ polynucleotide" is meant to include any polynucleotide having substantial identity to a nucleotide sequence of SEQ ID NO:1 or SEQ ID NO:3 or a fragment, variant, or analog thereof, as well as any polynucleotide encoding a polypeptide having substantial identity to the amino acid sequence of SEQ ID NO:2 or a fragment or variant thereof. Thus "RAQ polynucleotide" is meant to refer to RAQ RNA, cDNA, RAQ genomic DNA, and fragments, variants, and analogs thereof, as well as polynucleotides encoding RAQ polypeptide fragments or variants, unless specifically indicated otherwise.

"RAQ polypeptide" is meant to include any polypeptide having substantial identity to the amino acid sequence of SEQ ID NO:2 or a fragment, variant, or analog thereof, or a polypeptide encoded by a polynucleotide having substantial identity to the nucleotide sequence of SEQ ID NO:1 or SEQ ID NO:3 or a fragment, variant, or analog thereof. "RAQ polypeptide" is meant to refer to the full-length polypeptide, as well as fragments, variants, and analogs thereof, particularly those that retain biological activity, (e.g., biologically active fragments (e.g., fragments corresponding to functional domains such as GTP-binding domains), fusion proteins comprising all or a portion of a RAQ polypeptide, and the like) unless specifically indicated otherwise.

"Substantial identity", when referring to the RAQ polynucleotides of this invention, means polynucleotides having at least about 80%, typically at least about 90% and preferably at least about 95% sequence identity to the nucleotide sequence of SEQ ID NO: 1 or SEQ ID NO:3. Sequence identity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403–10. For the purposes of the present application, percent identity for the polynucleotides of the invention is determined using the BLASTN program with the default settings as described at http://www.ncbi.nlm.nih.gov/cgi-bin/BLAST/nph-newblast?Jform=0 with the DUST filter selected. The DUST filter is described at http://www.ncbi.nlm.nih.gov/BLAST/filtered.html. For a discussion of the sequence identity of Rho subfamily members, see Kahn et al. (1992) *FASEB J.* 6:2512–3. For a discussion of the sequence identity of Ras superfamily and subfamily members, see Kahn et al. (1992) *FASEB J.* 6:2512–3.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). By using probes, particularly labeled probes of DNA sequences, one can isolate homologous or related genes. The source of homologous genes may be any species, e.g. primate species particularly human; rodents, such as rats and mice, canines, felines, bovines, ovines, equines, yeast, Drosophila, Caenhorabditis, etc.

Substantial identity, when referring to the RAQ polypeptides of the invention are polypeptides having at least about 70%, typically at least about 80% and preferably at least about 90% to about 95% identity to the amino acid sequence of SEQ ID NO: 2, or that are encoded by polynucleotides which will hybridize under stringent conditions to a polynucleotide having the nucleotide sequence of SEQ ID NO:1 or SEQ ID NO:3. Percent identity for the polypeptides of the invention is determined using the BLASTP program with the default settings as described at http://www.ncbi.nlm.nih.gov/cgi-bin/BLAST/nph-newblast?Jform=0 with the DUST filter selected. The DUST filter is described at http://www.ncbi.nlm.nih.gov/BLAST/filtered.html. For a discussion of the sequence identity of Rho subfamily members, see Kahn et al. (1992) *FASEB J.* 6:2512–3. For a discussion of the sequence identity of ras superfamily and subfamily members, see Kahn et al. (1992) *FASEB J.* 6:2512–3.

Accordingly, the RAQ polynucleotides and polypeptides of this invention include, without limitation, Raq polypeptides and polynucleotides found in primates, rodents, canines, felines, equines, nematodes, yeast and the like, and the natural and non-natural variants thereof.

"Biological activities" of a RAQ polypeptide include, but are not necessarily limited to, for example, regulatory or biochemical functions, (e.g., GTPase activity, GTP-binding, interaction with a polypeptide as in a signaling pathway, and the like), antigenic activity, to be bound by an immunoglobulin or T cell antigen receptor specific for a Raq polypeptide, and the like), structural motifs, and other activities associated with naturally occurring RAQ polypeptide.

"cDNA" means a polynucleotide having a nucleotide sequence corresponding to the wild-type mRNA, i.e., the same arrangement of exons and 3' and 5' non-coding regions. Normally mRNA species have contiguous exons, with the intervening introns, when present, removed by nuclear RNA splicing, to create a continuous open reading frame encoding a RAQ protein.

"Polypeptide fragment", when referring to RAQ polypeptides of the invention, means any portion of a RAQ polypeptide, preferably one that retains substantially the same biological activity as that of the polypeptide having the amino acid sequence of SEQ ID NO:2. Exemplary RAQ polypeptide fragments are RAQ polypeptide fragments corresponding to functional domains, e.g., GTP-binding domains, GTPase catalytic domains and the like, or a RAQ polypeptide (e.g., SEQ ID NO:2). Polypeptide fragments of the invention are typically greater than 8 amino acids, usually about 12 to 20 amino acids, more usually about 50 to 100 amino acids, generally 150 amino acids or more, up to at least about 90–95% of the full-length polypeptide. Of particular interest are polypeptide fragments that are greater than 189 amino acids (e.g., at least about 190 amino acids), usually about 190 amino acids, in length.

"Polynucleotide fragment," when referring to RAQ polynucleotides of the invention, means polynucleotide fragments that are useful as probes, primers, antisense sequences for inhibition of transcription and/or translation, as well as coding sequences for the production of RAQ polypeptides and fragments thereof, and the like. Of particular interest are polynucleotide fragments of the nucleotide sequence of SEQ ID NO:1 or SEQ ID NO:3. Polynucleotide fragments of the invention are typically greater than 567 nucleotides (e.g., at. least about 568 nucletodies), usually 521 to 600 nucleotides or 550 to 750 nucleotides, in size. Polynucleotide fragments of the RAQ coding sequence of interest are typically greater than 322 nucleotides (e.g., at least about 323 nucleotides), usually greater than 566 nucleotides up to the entire coding sequence.

"Genomic DNA" means a polynucleotide having substantially the same nucleotide sequence, i.e., the same initiation codon, the stop codon and all intervening exons and introns, present in a corresponding wild type chromosome. Of particular interest is a genomic sequence comprising the nucleic acid present between the initiation codon and the stop codon, as defined in the listed sequences, including all of the introns that are normally present in a native chromosome. Genomic DNA may include 3' and 5' untranslated regions found in mature mRNA. Genomic DNA may include transcriptional and translational regulatory sequences, such as promoters, enhancers, and the like, and may include approximately 1 kb, or more, of flanking genomic DNA at the 5' or 3' end of the transcribed region, i.e., sequences required for proper tissue and stage specific expression. Alternatively, the genomic DNA may comprise a fragment of 100 kbp, or less, and substantially free of flanking genomic DNA. The genomic DNA flanking the coding region, either 3' or 5', or internal regulatory sequences as sometimes found in introns, may contain sequences required for proper tissue and stage specific expression.

"Isolated" means separated from some or all other material present in the natural environment of the RAQ polynucleotide or RAQ polypeptide. For example, RAQ polynucleotides of the invention are generally isolated as other than an intact chromosome. Molecules so isolated can be introduced into vectors, host cells or whole organisms or occur in composition with other ingredients and still be considered isolated, as such term is used herein. Typically, RAQ polynucleotides and polypeptides of the invention are isolated in substantial purity. Substantial purity, when referring to polynucleotides, means generally at least about 50%, typically at least about 90%, pure. Substantial purity, when referring to polypeptides, means generally at least about 80%, typically at least about 90%, pure. RAQ polynucleotides of the invention include "recombinant" polynucleotides, i.e. a RAQ sequence flanked by one or more nucleotides with which it is not normally associated on a naturally occurring chromosome.

"Antigenic activity" means the capacity to elicit an immune response (e.g., B cell- or T cell-mediated response) and/or be bound by polypeptide-specific antibodies. (e.g., RAQ polypeptide-specific antibodies).

"Substantially the same biological activity" means that activity which would be considered meaningful, qualitatively and/or quantitatively, by one of ordinary skill in the relevant art.

"Variant" means a polynucleotide or polypeptide which differs from a provided polynucleotide or polypeptide by one or more residues (e.g., nucleotide residue or amino acid residue), and include polynucleotides or polypeptides having residue substitutions, deletions and/or insertions relative to a reference polynucleotide or polypeptide sequence. "Naturally occurring variants" means polynucleotides and polypeptides derived from natural sources and "non-natural variants" means variants that have been artificially produced. For example, non-natural variants may differ from the polynucleotide or polypeptide referred to by at least two, but not more than about ten, nucleotides or amino acids. In general, "variants" refers to polynucleotides or polypeptides that are changed in their sequence relative to a reference sequence, but that have substantially no change in the chemical composition of the individual residues or the backbone of the molecule.

"Analog" means a polynucleotide or polypeptide that differs from a provided polynucleotide or polypeptide due to the presence of modifications in the chemical composition of one or more residues (e.g., an amino acid residue or a nucleotide residue) and/or modifications to the chemistry of the backbone of the molecule. Analogs of amino acids and polynucleotides, and methods of production of same, are well known in the art. Chemical "derivatives" (e.g., as "derivative" is used in the chemical arts) are meant to be encompassed by the use of the term "analog" in accordance with the invention.

For example, the polynucleotides of the invention can be modified so as to contain synthetic nucleotide analogs. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate analogs include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The a-anomer of deoxyribose may be used, where the base is inverted with respect to the natural b-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

The term "wild-type" may be used to refer to the most common allele in a population. It will be understood by one of skill in the art that the designation as "wild-type" is merely a convenient label for a common allele, and should not be construed as conferring any particular property on that form of the sequence.

Preferred Embodiments

While the broadest definition of this invention is set forth in the Summary of the invention, certain aspects of the invention are preferred. A preferred aspect of the invention are isolated RAQ polynucleotides selected from (I) polynucleotides having substantial identity to a nucleotide sequence of SEQ ID NO:1 or SEQ ID NO:3 and (ii) polynucleotides encoding polypeptides having substantial identity to an amino acid sequence of SEQ ID NO:2. Particularly preferred are those RAQ polynucleotides having the nucleotide sequence of SEQ ID NO:1 or SEQ ID NO:3 and those RAQ polynucleotides encoding a polypeptide having the amino acid sequence of SEQ ID NO:2.

A preferred aspect of the invention are isolated RAQ polypeptides selected from (I) polypeptides having substantial identity to the amino acid sequence of SEQ ID NO:2 and (ii) polypeptides encoded by polynucleotides having substantial identity to the nucleotide sequence of SEQ ID NO:1 or SEQ ID NO:3; and fragments, variants, and analogs thereof. Particularly preferred are those RAQ polypeptides having the nucleotide sequence of SEQ ID NO:2 and those RAQ polypeptides encoded by polynucleotides having the nucleotide sequence of SEQ ID NO:1 or SEQ ID NO:3; and fragments, variants, and analogs thereof.

Characterization of RAQ

Human RAQ polynucleotides of the invention comprise the nucleotide sequence of SEQ ID NO:1, SEQ ID NO:3, and fragments, variants, and analogs thereof. The human gene sequence is provided as SEQ ID NO:3, and the encoded polypeptide product as SEQ ID NO:2. The longest open reading frame (ORF) of the human gene encodes a 199 amino acid polypeptide, and is encoded by the sequence provided as SEQ ID NO:1.

The amino acid sequence of SEQ ID NO:2 is consistent with the primary structure of a GTP-binding protein, such as those within the Ras GTPase subfamily. In this regard, the four conserved GTP-binding domains characteristic of GTP-binding proteins are found in the RAQ polypeptides of the invention (FIG. 2, domains I, III, IV, and V). RAQ also contains an amino acid sequence corresponding to, but not identical to, the conserved effector domain (FIG. 2, II). Without being held to theory, the presence of this domain suggests that RAQ may interact with some of the same effectors as Ras, but may also interact with different downstream effectors. RAQ shares the highest level of amino acid sequence identity (approximately 50% identity) with the human Ras-related proteins R-ras2, Rin, Rit, RaIA, and Rap1b, and with the *D. discoideum* proteins RasS and RasD: Like Rit and Rin, RAQ lacks the C-terminal CAAX domain, which is present in the majority of Ras subfamily members. The CAAX domain is used by the posttranslational processing enzyme farnesyltransferase to direct the protein to the plasma membrane. Since Rit and Rin lack the CAAX domain but are nevertheless membrane-associated proteins, it is likely that posttranslational processing of Rit and Rin occurs through a mechanism different from farnesyltransferase. Given the homologies described above, RAQ may also undergo posttranslational processing through a unique pathway, thus providing a specific target for intervention in RAQ activity in the cell.

The human RAQ gene is localized to 12p12-13. Hence, the RAQ gene of this invention represents a novel proto-oncogene of which alterations may be associated with cancers linked to the 12p12-13 region. Mutations in the 12p12-13 region have been reported in various tumor types, including pancreatic, gynecological (e.g., ovarian), small bowel and colorectal. Furthermore, because RAQ is within the same cytoband as the human K-ras gene (Johansson et al. (1993) *Genes, Chromosomes, Cancer.* 8:205–218; Hatta et al. ((1997) *Br J Cancer.* 75(9):1256–1262; Manenti et al. (1997) *Carcinogenesis* 18(10):1917–1920.; Cave et al. (1995) *Blood* 86:3869–75), the RAQ gene may underlie certain of the cytogenetic abnormalities and tumor linkages observed on chromosome 12p. Mutations which constitutively activate RAQ or which delete RAQ resulting in inactivation or partial inactivation, may play a role in perturbing the native function that RAQ plays in cellular proliferation and thus promotes abnormal cell growth. Moreover, alterations in RAQ, rather than alterations in K-ras, may be associated with cancers that have been previously associated with undefined mutations in the 12p12-13 region. Accordingly, the polynucleotides and polypeptides of the Invention are useful for detecting in an individual the presence of a genetic polymorphism of a RAQ gene associated with a disease state or genetic predisposition to a disease state. Polymorphisms associated with disease states or genetic predispositions to a disease state include, without limitation, deletion or truncation of the gene and mutations that affect gene expression, the affinity of the RAQ polypeptide for GTP and/or the GTPase activity of the RAQ polypeptide.

Fragments comprising the RAQ polynucleotides of the invention are useful as primers for PCR, probes in hybridization screening, and the like. The polynucleotides of the invention also can be used as probes in identifying the level of expression of the RAQ gene in biological specimens. Such methods are well known in the art. In short, DNA or mRNA is isolated from a cell sample, mRNA is amplified by RT-PCR or separated by gel electrophoresis, and probed with a fragment of the RAQ polynucleotide. Oligonucleotide ligation, in situ hybridization and solid chip DNA array techniques also may be used.

Polynucleotides comprising the 5'-flanking region of the RAQ gene are useful for their promoter elements, including enhancer binding sites. For example, the sequence of the 5' flanking region may be utilized for promoter elements, including enhancer binding sites, that provide for developmental regulation in tissues where RAQ is expressed. The tissue specific expression is useful for determining the pattern of expression, and for providing promoters that mimic the native pattern of expression. Naturally occurring variants of polynucleotides containing the promoter region can be used to determine polymorphisms in RAQ gene expression that are associated with a particular disease. Methods for the identification of specific DNA motifs involved in the binding of transcriptional factors are known in the art, e.g. sequence similarity to known binding motifs, gel retardation studies, etc. For examples, see Blackwell et al. (1995), *Mol. Med.* 1:194–205; Mortlock et al. (1996), *Genome Res.* 6:327–33; and Joulin and Richard-Foy (1995), *Eur. J. Biochem.* 232:620–626.

The regulatory sequences of RAQ may be used to identify cis acting sequences required for transcriptional or translational regulation of RAQ expression, especially in different tissues or stages of development, and to identify cis acting sequences and trans-acting factors that regulate or mediate RAQ expression. Such transcription or translational control regions may be operably linked to a RAQ gene in order to promote expression of wild type or altered RAQ or other proteins of interest in cultured cells, or in embryonic, fetal or adult tissues, and for gene therapy.

Variants of RAQ polynucleotides can be used to, for example, detect alteration of expression in experimentally defined systems, and other uses that will be readily apparent to one of ordinary skill in the art. For example, variants include polynucleotide sequences having mutations introduced into a promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626. Exemplary variants useful in detection of alteration of RAQ expression include fusion proteins comprising FLAG™ epitope tags or green fluorescent protein sequences.

Preparation of RAQ Polynucleotides

Polynucleotides encoding RAQ may be cDNA, genomic DNA, or a fragment, variant, or analog thereof, and can be prepared by methods known to those of ordinary skill in the art provided with the information of the present application. For example, cDNA libraries can be screened with hybridization probes designed to complement a portion of the nucleotide sequence of SEQ ID NO:1 or SEQ ID NO:3. Suitable probes will be of approximately 18 nucleotides to the full length of the gene, more typically approximately 30 nucleotides in length. Low stringency conditions, e.g., 50° C. and 6×SSC (0.9 M saline/0.09 M sodium citrate) are used to identify and isolate RAQ polynucleotides having nucleotide sequences similar to that of the probe. High stringency conditions, e.g., 50° C. or higher and 0.1×SSC (15 mM saline/1.5 mM sodium citrate) are used to identify and isolated RAQ polynucleotides having nucleotides essentially identical to that of the probe. The RAQ polynucleotides may be introduced into an appropriate vector for extrachromosomal maintenance or for integration into a host genome.

The RAQ polynucleotides of the invention may be obtained as double or single stranded fragments by conventional means, i.e., chemical synthesis, restriction enzyme digestion, PCR amplification, and the like. For the most part, small DNA fragments, such as those useful as primers for PCR, hybridization screening probes, etc., will be of at least 15 nt, usually at least 18 nt or 25 nt, and may be at least about 50 nt. PCR amplification requires a pair of primers, typically a pair which will generated an amplification product of at least 50 nucleotides, preferably at least 100 nucleotides in length. Suitable primers hybridize to the target polynucleotide under stringent conditions. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Software designed for selecting suitable sequences for primers are commercially available. Larger DNA fragments, i.e. greater than 100 nt are useful for production of the encoded polypeptide.

Variants of RAQ polynucleotides of the invention can be prepared by methods known in the art. For example, techniques for site specific in vitro mutagenesis are found in Gustin et al. (1993) *Biotechniques* 14:22; Barany (1985), *Gene* 37:111–23; Colicelli et al. (1985), *Mol. Gen. Genet.* 199:537–9; and Prentki et al., (1984), *Gene* 29:303–13. *Molecular Cloning: A Laboratory Manual*, CSH Press 1989, pp 15.3–108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4.

The resulting variants may, for example, contain mutations in the RAQ gene sequence, which may include flanking promoter regions and coding regions. Variants of the invention may include variants having targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc., as well as production of fusion proteins, e.g., using green fluorescent proteins (GFP). For example, a GST (Glutathione S-Transferase) fusion protein of RAQ can be prepared using the pGEX vector (Pharmacia) encoding the full length 199 residue Raq protein. The resulting fusion protein can be purified using the GST-moiety, and the purified protein used in assays to test the intrinsic GTPase activity of RAQ using radiolabeled P32-γ- GTP retention assays as described (Lee et al. (1996) *J. Neurosci.* 16(21):6784–94.

RAQ Polypeptides

The RAQ polypeptides of this invention can be prepared by methods known to those of ordinary skill in the art relying upon their personal knowledge and the information provided in this application. For example, the polynucleotides of the Invention can be used to construct expression vectors, and can be used to produce all or a portion of RAQ polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a RAQ gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. -galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

RAQ polypeptides may be expressed in prokaryotes or eukaryotes in accordance with conventional ways, depending upon the purpose for expression. For large scale production of the protein, a unicellular organism, such as *E. coli*, *B. subtilis*, *S. cerevisiae*, insect cells in combination with baculovirus vectors, or cells of a higher organism such as vertebrates, particularly mammals, e.g. COS 7 cells, may be used as the expression host cells. In some situations, it is desirable to express the RAQ gene in eukaryotic cells, where the RAQ protein will benefit from native folding and post-translational modifications. Small peptides can also be synthesized in the laboratory. Polypeptides that are subsets of the complete RAQ sequence may be used to identify and investigate parts of the protein important for function, such as the GTP binding domain(s), or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed RAQ polypeptides are useful for the production of antibodies, where short fragments provide for antibodies specific for the particular polypeptide, and larger fragments or the entire protein allow for the production of antibodies over the surface of the polypeptide. Antibodies may be raised to the wild-type or variant forms of RAQ. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Identification of RAQ-Related Sequences

Homologs of RAQ are identified by any of a number of methods. A fragment of the provided cDNA may be used as a hybridization probe against a cDNA library from the target organism of interest, where low stringency conditions are used. The probe may be a large fragment, or one or more short degenerate primers.

Nucleic acids having sequence similarity are detected by hybridization under low stringency conditions, for example, at 50° C. and 6×SSC (0.9 M saline/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided RAQ sequences, e.g. allelic variants, genetically altered versions of the gene, etc., bind to the provided RAQ sequences under stringent hybridization conditions. By using probes, particularly labeled probes of DNA sequences, one can isolate homologous or related genes. The source of homologous genes may be any species, e.g., primate species, particularly human; rodents, such as rats and mice, canines, felines, bovines, ovines, equines, yeast, nematodes, etc.

Between mammalian species, e.g., human and mouse, homologs have substantial sequence similarity, e.g. at least 75% to 80% sequence identity, usually at least 90%, more usually at least 95% identity between nucleotide sequences.

Sequence identity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. The sequences provided herein are essential for recognizing RAQ-related and homologous proteins in database searches.

Detection of RAQ Expression

The DNA of the invention may be used to identify expression of the RAQ gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of RAQ gene expression in the sample.

Diagnostic Uses

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a RAQ coding region or control regions is associated with disease, particularly cancers, e.g. lung cancer, germ cell cancers, and cancers involving eosinophils. Disease associated polymorphisms may include deletion or truncation of the gene, mutations that alter expression level, that affect the activity of the protein in binding to GTP, GTPase activity, etc.

Changes in the promoter or enhancer sequence that may affect expression levels of RAQ can be compared to expression levels of the normal allele by various methods known in the art. Methods for determining promoter or enhancer strength. include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express RAQ may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N', N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type RAQ sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Preferably, such arrays comprise at least one, preferably two or more probes for detection of RAQ locus polymorphisms, where the probes comprise at least one form of a polymorphic sequence of SEQ ID NO:1 and/or 3, or a fragment thereof.

Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in RAQ may be based on the functional or antigenic characteristics of the protein. Protein truncation assays are useful in detecting deletions that may affect the biological activity of the protein. Various immunoassays designed to detect polymorphisms in RAQ proteins may be used in screening. Where many diverse genetic mutations lead to a particular disease phenotype, functional protein assays have proven to be effective screening tools. The activity of the encoded RAQ protein in GTP binding, GTPase activity, etc., may be determined by comparison with the wild-type protein.

Antibodies specific for a RAQ may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal RAQ in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Diagnostic screening may also be performed for polymorphisms that are genetically linked to a disease predisposition, particularly through the use of microsatellite markers or single nucleotide polymorphisms. Frequently the microsatellite polymorphism itself is not phenotypically expressed, but is linked to sequences that result in a disease predisposition. However, in some cases the microsatellite sequence itself may affect gene expression. Microsatellite linkage analysis may be performed alone, or in combination with direct detection of polymorphisms, as described above. The use of microsatellite markers for genotyping is well documented. For examples, see Mansfield et al. (1994), *Genomics* 24:225–233; Ziegle et al. (1992), *Genomics* 14:1026–1031; Dib et al., supra.

Modulation of RAQ Gene Expression

The RAQ genes, gene fragments, or the encoded RAQ protein or protein fragments are useful in gene therapy to treat disorders associated with RAQ defects. Expression vectors may be used to introduce the RAQ gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or RAQ protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the RAQ DNA, then bombarded into skin cells.

Antisense molecules can be used to down-regulate expression of RAQ in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences. In addition to their use in alteration of gene expression, sense or antisense synthetic ODN may also be used as probes.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

Genetically Altered Cell or Animal Models for RAQ Function

The subject nucleic acids can be used to generate transgenic, non-human animals or site specific gene modifications in cell lines. Transgenic animals may be made through homologous recombination, where the normal raq locus is altered. Alternatively, a nucleic acid construct is randomly integrated into the genome. Vectors for stable integration include plasmids, retroviruses and other animal viruses, YACs, and the like.

The modified cells or animals are useful in the study of raq function and regulation. For example, a series of small deletions and/or substitutions may be made in the host's native raq gene to determine the role of different exons in oncogenesis, signal transduction, etc. Of interest are the use of raq to construct transgenic animal models for cancer, where expression of Raq is specifically reduced or absent. Specific constructs of interest include anti-sense raq, which will block Raq expression, expression of dominant negative raq mutations, and over-expression of Raq genes. Where a raq sequence is introduced, the introduced sequence may be either a complete or partial sequence of a raq gene native to the host, or may be a complete or partial raq sequence that is exogenous to the host animal, e.g., a human RAQ sequence. A detectable marker, such as lac Z may be introduced into the raq locus,, where upregulation of raq expression will result in an easily detected change in phenotype.

One may also provide for expression of the raq gene or variants thereof in cells or tissues where it is not normally expressed, at levels not normally present in such cells or tissues, or at abnormal times of development. By providing expression of Raq protein in cells in which it is not normally produced, one can induce changes in cell behavior, e.g. through Raq-mediated intracellular signaling.

DNA constructs for homologous recombination will comprise at least a portion of the human RAQ gene or of a raq gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and, analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on Ras or related gene activation, oncogenesis, etc.

In Vitro Models for RAQ Function

The availability of a number of components in the Ras signaling pathway, as previously described, allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other; utilization of GTP, etc. The components may be modified by sequence deletion, substitution, etc. to determine the functional role of specific domains.

Drug screening may be performed using an in vitro model, a genetically altered cell or animal, or purified RAQ protein. One can identify ligands or substrates that bind to, modulate or mimic the action of RAQ. Areas of investigation include the development of cancer treatments, metastasis, etc. The relationship between RAQ, Ras and Ras-related proteins suggests that agents that modulate each of these protein activities will have antagonistic activities.

Drug screening identifies agents that provide a replacement for RAQ function in abnormal cells. Agents that inhibit its function, in terms of induction of cellular proliferation or differentiation, are predicted to inhibit the process of oncogenesis. Conversely, agents that mimic RAQ function may stimulate controlled growth and healing, or may stimulate a cellular developmental pathway. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, such as GTP binding, etc.

The term "agent" as used herein describes any molecule, e.g. protein or pharmaceutical, with the capability of altering or mimicking the physiological function of RAQ. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic RAQ function, such as GTP binding properties, GTPase activity, etc. For example, an expression construct comprising a RAQ gene or a constitutively activated RAQ polypeptide may be introduced into a cell line under conditions that allow expression. The level of RAQ activity is determined by a functional assay, as previously described. In one screening assay, candidate agents are added in combination with GTP, and activity in conversion of GTP to GDP is detected. In another assay, the ability of candidate agents to inhibit or enhance RAQ function is determined. Alternatively, candidate agents are added to a cell that lacks functional RAQ, and screened for the ability to reproduce RAQ in a functional assay.

The compounds having the desired pharmacological activity may be administered in a physiologically acceptable carrier to a host for treatment of cancer, etc. The compounds may also be used to enhance RAQ function in, for example, wound healing, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Summary of Exemplary Uses of RAQ Polynucleotides and Polypeptides

As indicated above, nucleic acid compositions encoding RAQ can be used for a variety of purposes, include, but not necessarily limited to identification of homologous or related genes; production of compositions that modulate the expression or function of its encoded protein; administration in gene therapy; mapping functional regions of the protein; and study of associated physiological pathways. Modulation of RAQ gene activity in vivo may be used for prophylactic and therapeutic purposes, such as treatment of cancer, investigation of Ras signaling pathway function, identification of cell type based on expression, and the like. The protein is useful as an immunogen for producing specific antibodies, in screening for biologically active agents that act in the Ras signaling pathway and for therapeutic and prophylactic purposes. Uses additional to or that are variations of the uses described herein will be readily appreciated by the ordinarily skilled artisan upon reading the present specification.

EXAMPLES

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for.

Example 1

Preparation of RAQ Polynucleotides

The GenBank expressed sequence tag (EST) database (http://www.ncbi.nlm.nih.gov/BLAST/blast_databases.html) was searched for ESTs showing similarity to 43 known Ras-related proteins (see Table 2) using the "basic local alignment search tool" program, TBLASTN, with default settings as described at (http://www.ncbi.nlm.nih.gov/BLAST/blast_help.html). Human ESTs identified as having similarity to these known Ras-related (defined as p<0.0001) were used in a BLASTN and BLASTX screen of the GenBank non-redundant (NR) database (http://www.ncbi.nlm.nih.gov/BLAST/blast_databases.html) using default settings as described (http://www.ncbi.nlm.nih.gov/BLAST/blast_help.html).

of the UniGene database revealed that the 5' EST of the 649419 IMAGE clone represented a novel human gene.

The 649419 IMAGE clone was sequenced using standard ABI dye-primer and dye-terminator chemistry on a 377 automatic DNA sequencer. Sequencing revealed that the 649419 IMAGE clone corresponds to nucleotides 406 to 2309 of SEQ ID NO: 3. Analysis of this gene fragment revealed that the gene product is a novel Ras-related GTP-binding protein, thereafter termed RAQ. A BLASTX comparison of the 649419 full length nucleotide sequence revealed that the first residue of the deduced protein was a phenylalanine and it did not possess a start methionine. Thus, the 649419 IMAGE clone did not contain the 5' end of the coding sequence.

Walking primers were designed to obtain the full length double stranded IMAGE clone consensus sequence, which contained a polyA tail. Gene specific oligodeoxynucleotide primers (i.e., 649419-1, 5'-GTCGGTAGGTTGATT CGAGGGTGG-3' (SEQ ID NO:4); 649419-2, 5'-TCATATTCCCAGATGAACCGTTTG-3' (SEQ ID NO:5); and 649419-3, 5'-TCTCACTACAAGAGC TGACTTGCC-3' (SEQ ID NO:6)) were designed and then

TABLE 2

List of the ras-subfamily peptide used in database mining

| Probe Source | Swissprot# | Probe Source | Swissprot# | Probe Source | Swissprot# |
|---|---|---|---|---|---|
| rash_rat | P20171 | ras_artsa | P18262 | rras_mouse | P010833 |
| rash_human | P01112 | lt60_caeel | P22981 | rras_human | P10301 |
| rash_msvns | P23175 | rasg_dicdi | P15063 | ras3_drome | P08645 |
| rash_chick | P08642 | rasl_neucr | P22126 | rapb_human | P09526 |
| rash_msv | P01113 | ras3_rhira | P22280 | rapa_disom | P22123 |
| rash_msvha | P01115 | ras1_rhira | P22278 | rapa_human | P10113 |
| rask_human | P01116 | ras_schpo | P08647 | rap1_dicdi | P18613 |
| rasl_human | P01118 | ras_lened | P28775 | rala_human | P11233 |
| rasl_mouse | P08643 | rasb_dicdi | P32252 | ral_calja | P05810 |
| ras_carau | P05774 | ras2_yeast | P01120 | ral_disom | P22124 |
| rask_mouse | P32883 | rasc_dicdi | P32253 | ralb_human | P11234 |
| rasn_cavpo | P12825 | ras1_yeast | P01119 | rsr1_yeast | P13856 |
| rasn_human | P01111 | ras2_drome | P04388 | ras_geocy | P24498 |
| rask_msvki | P01117 | rtc1_human | P17082 | rap2_human | P10114 |
| rask_rat | P08644 | rass_dicdi | P32254 | rap3_human | P17964 |
| ras1_drome | P08646 | ras2_rhira | P22279 | | |

ESTs that had top human hits with >95% identity over 100 amino acids were discarded. This was based upon the inventors' experience that these sequences were usually identical to the starting probe sequences, with the differences due to sequence error. The remaining BLASTN and BLASTX outputs for each EST were examined manually, i.e., ESTs were removed from the analysis if the inventors determined that the variation from the known Ras-related probe sequence was a result of poor database sequence. Poor database sequence was usually identified as a number of 'N' nucleotides in the database sequence for a BLASTN search and as a base deletion or insertion in the database sequence, resulting in a peptide frameshift, for a BLASTX output. ESTs for which the highest scoring match was to non-Ras-related sequences were also discarded at this stage.

Analysis of the BLASTN and BLASTX outputs identified a 311 nucleotide EST sequence from the 5' end of the IMAGE clone 649419 that had potential for being associated with a sequence encoding a novel Ras-related GTP-binding, e.g., the sequence had homology, but not identity, to known ras-related proteins. The reported nucleotide sequence of the 5' EST of the 649419 IMAGE clone corresponds approximately to nucleotides 406 to 717 of SEQ ID NO:3. A search used to construct full length RAQ cDNA by 5 prime RACE (rapid amplification of DNA ends; Frohman et al. 1988, Proc. Natl. Acad. Sci USA 85:8898–9002). A nested primer strategy was used on fetal brain cDNA provided With a Marathon-Ready™ RACE kit (Clontech, Palo Alto, Calif.).

The product so obtained comprised a RAQ polynucleotide having a nucleotide sequence of SEQ ID NO:3, which contained an additional 405 nucleotides in the 5'-untranslated region, including the start codon and a TAA termination codon 23 bp further upstream. BLASTX analysis indicated that the starting methionine residue was present at nucleotides 374–376 and that an upstream in-frame stop codon was present at nucleotides 287–289. The full length mRNA sequence for RAQ was 2309 nucleotides in length (SEQ ID NO:3), and the longest ORF (SEQ ID NO:1; bold sequence in FIG. 1A) predicted a protein of 199 amino acids (SEQ ID NO:2), as shown in FIGS. 1A and 1B.

Example 2

Chromosomal Localization of the RAQ Gene

Two primers (i.e., 649419.RHF, 5'-GGATTCTGAGAA ATGTCTGG-3', SEQ ID NO:7; and 649419.RHR, 5'-TCATTTCAGAATCTCTGGTG-3', SEQ ID NO:8) were designed in the 3'-untranslated region to amplify a product across the Stanford G3 radiation hybrid map. The PCR data were submitted for automatic two-point analysis. Mapping data were correlated with cytoband information and comparisons with the OMIM human gene map data base were made.

Results indicated that the RAQ gene is located approximately 13.31 cR away from the framework marker SHGC-11783 corresponding to cytoband 12p12-13 and, thus, in the same cytoband as the human K-ras gene.

Example 3

Expression Analysis of RAQ

A probe was created from an EcoRI fragment corresponding to nucleotides 406 to 1546 of SEQ ID NO:3 and purified fragment was labeled with [$^{32}$P]dCTP Amersham) by the random primer method. Adult human Multiple Tissue Northern MTM™) Blots (Clontech) were hybridized with the [$^{32}$P]-labeled fragment in ExpressHyb™ solution (Clontech) for four hours, washed to a final stringency of 0.1×SSC, 0.1% SDS at 65° C. and subjected to autoradiography for 24 hours.

Analysis revealed that RAQ is expressed in multiple adult tissues, though not ubiquitously, as a single approximately 2.3 kb mRNA. Expression levels are high in heart, placenta, kidney, pancreas, spleen, ovary, stomach and adrenal gland, moderate in brain, spinal cord, prostate, testis, colon, small intestine, thyroid and trachea and low in lung skeletal muscle, lymph node and bone marrow. No RAQ mRNA was detectable on these Northern blots for liver, thymus, and peripheral blood leucocytes, indicating either a very low level of expression or that RAQ is not expressed in these tissues.

Example 4

Analysis of RAQ Polypeptide Sequence

The alignment of the RAQ polypeptide sequence with its most closely related proteins is shown in FIG. 2. Dots in FIG. 2 represent spaces to optimize alignment. Residues occurring in 7 or more of these proteins are capitalized and comprise the consensus sequence. The five conserved domains characteristic of small GTP-binding proteins are underlined; I, III, IV and V are GTP-binding domains; II is the effector loop. RAQ shares the highest level of peptide identity (~50%) with the human ras-related proteins; R-ras2 (TC21), Rin, Rit, RaIA and Rap1b (Drivas et al. (1990), supra; Lee et al. (1996), supra; Kawasaki et al. 1997, GENPEPT report, accessible at Genbank #U78166; Hall and Zerial (1995), supra and with the D. discoideum proteins RasS and RasD.

The four conserved GTP-binding domains found in small GTPase proteins are present within the RAQ polypeptide sequence, predicting its GTPase activity. The effector domain of Rap1b is identical to that of H-, K- and N-ras and is important in determining its interactions with other signaling molecules such as Raf (Boguski and McCormick (1993) Nature 366:643–654). The effector domain of RaIA differs by only 1 amino acid, but in other human proteins in this alignment, including RAQ, this domain differs more significantly, indicating that although these proteins may interact with some of the same effectors as ras, there is potential for interaction with different downstream effectors.

In contrast to the majority of members of the Ras-subfamily, RAQ shares the property, with Rit and Rin, of not possessing a C-terminal CAAX domain. This domain is used in the posttranslational processing of Ras proteins prior to membrane association. Despite its absence Rit and Rin have been demonstrated to be membrane associated, though the mechanism underlying this localization remains unclear (Lee et al. (1996) supra). Farnesyltransferase is a posttranslational processing enzyme which utilizes the CAAX motif in the process of directing ras to the plasma membrane. One line of investigative tumor therapy utilizes a variety of natural products and synthetic compounds to block the farnesylation of ras (and its subsequent membrane localization), by farnesyltransferase (Omer et al. (1997) *Biofactors* 6:359–66). If like Rin and Rit, RAQ is also shown to associate with the membrane, perhaps utilizing a different enzymatic mechanism, there may be potential for a specific point of intervention of active RAQ in the cell.

Example 5

Phylogenetic Analysis of RAQ Sequence

To assess how RAQ is related to other small GTPase proteins a phylogenetic tree prepared (FIG. 3). The RAQ sequence was compared to the following sequences: Rin (human, Genbank accession #=Y07565), Rit (human, Genbank accession #=U71203), TC21 (human, pid=g2507282), Rap1b (human, Swissprot #=P09526), RaIA (human, Genbank accession #=X15014), Kras (human, Genbank accession #=M54968), Hras (human, Genbank accession #=J00277), Rras (human, Swissprot#=P10301), Rap2a (human, Swissprot#=P10114), from the rho-subfamily; RhoA, (human, pid #g68960), from the rab subfamily; Rab3c,. (rat, Genbank accession #=Y14019), and the ran-subfamily; Ran (human, pid#=g2144602). The tree was generated using the ClustalwPPC program (Macintosh format).

This analysis indicates that RAQ is a member of the ras-subfamily of small GTPases, not the rho, rab or ran subfamilies. Though RAQ is most closely related to Rit and Rin, it does form its own branch of the tree and therefore may represent a novel group of proteins within the ras-subfamily.

All publications and patent applications cited in this specification are herein incorporated by reference as if each individual publication or patent application were specifically and individually indicated to be incorporated by reference. The publications discussed herein are provided solely for their disclosure prior to the filing date of the present application. Nothing herein is to be construed as an admission that the invention is not entitled to antedate such a disclosure by virtue of prior invention.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated mammalian RAQ polypeptide having an amino acid sequence as set forth in SEQ ID NO:2, wherein said RAQ polypeptide has guanosine triphosphate (GTP) binding activity.

\* \* \* \* \*

SEQUENCE LISTING

<160> NUMBER OF SEQ ID NOS: 16

<210> SEQ ID NO 1
<211> LENGTH: 600
<212> TYPE: DNA
<213> ORGANISM: Homo sapiens

<400> SEQUENCE: 1

```
atggctaaaa gtgcggaggt caaactggca atatttggga gagcaggcgt gggcaagtca      60
gctcttgtag tgagatttct gaccaaacgg ttcatctggg aatatgatcc caccctcgaa     120
tcaacctacc gacaccaagc aaccatcgat gatgaagttg tttccatgga gatactagac     180
actgctggtc aggaagatac cattcagagg gaggggcaca tgcgatgggg ggaaggcttt     240
gtgctggtct acgacattac tgaccgagga agttttgagg aagtgctgcc acttaagaac     300
atcctagatg agatcaaaaa gcccaagaat gtgactctca tcttggttgg aaacaaagct     360
gacttggacc actccaggca ggttagcaca gaagaaggag agaagctggc cacagaattg     420
gcttgtgctt tttacgagtg ctctgcctgc actggagaag ggaatatcac agagatattc     480
tatgaattgt gtcgagaggt gcgtcgccgg aggatggtgc agggcaagac gaggcgacgc     540
agctccacca cgcatgtcaa gcaagccatt aacaagatgc tcaccaaaat cagtagttag     600
```

<210> SEQ ID NO 2
<211> LENGTH: 199
<212> TYPE: PRT
<213> ORGANISM: Homo sapiens

<400> SEQUENCE: 2

```
Met Ala Lys Ser Ala Glu Val Lys Leu Ala Ile Phe Gly Arg Ala Gly
  1               5                  10                  15

Val Gly Lys Ser Ala Leu Val Val Arg Phe Leu Thr Lys Arg Phe Ile
             20                  25                  30

Trp Glu Tyr Asp Pro Thr Leu Glu Ser Thr Tyr Arg His Gln Ala Thr
         35                  40                  45

Ile Asp Asp Glu Val Val Ser Met Glu Ile Leu Asp Thr Ala Gly Gln
     50                  55                  60

Glu Asp Thr Ile Gln Arg Glu Gly His Met Arg Trp Gly Glu Gly Phe
 65                  70                  75                  80

Val Leu Val Tyr Asp Ile Thr Asp Arg Gly Ser Phe Glu Glu Val Leu
                 85                  90                  95

Pro Leu Lys Asn Ile Leu Asp Glu Ile Lys Lys Pro Lys Asn Val Thr
            100                 105                 110

Leu Ile Leu Val Gly Asn Lys Ala Asp Leu Asp His Ser Arg Gln Val
        115                 120                 125

Ser Thr Glu Glu Gly Glu Lys Leu Ala Thr Glu Leu Ala Cys Ala Phe
    130                 135                 140

Tyr Glu Cys Ser Ala Cys Thr Gly Glu Gly Asn Ile Thr Glu Ile Phe
145                 150                 155                 160

Tyr Glu Leu Cys Arg Glu Val Arg Arg Arg Met Val Gln Gly Lys
                165                 170                 175

Thr Arg Arg Arg Ser Ser Thr Thr His Val Lys Gln Ala Ile Asn Lys
            180                 185                 190

Met Leu Thr Lys Ile Ser Ser
        195
```

<210> SEQ ID NO 3
<211> LENGTH: 2309
<212> TYPE: DNA
<213> ORGANISM: Homo sapiens

<400> SEQUENCE: 3

```
tcactatagg gctcgagcgg ccgcccgggt aggtccgcag tccctccgcc gctagtcgga      60
gcgagcgcga gtgaggagac ccccgccggg ccactggcac ttgcttctgc ggcgagtccc     120
acccacgacc gcagcccagc aactcgcaaa cgcaacctga agcctgggct gcgcagtgtg     180
ggagggcttc gcgatcttgg gggacccatt ccgaacttgc agaggaccgt agctctcctg     240
gcctggagag tgtgaacagg attgtggact cttccaagat tcacaatgat atggtgaatc     300
caaagactgg aaccaaaaag atttactcag tgctttagtt ttaacaacag taaattgtct     360
accaacaccc atcatggcta aaagtgcgga ggtcaaactg gcaatatttg ggagagcagg     420
cgtgggcaag tcagctcttg tagtgagatt tctgaccaaa cggttcatct gggaatatga     480
tcccacccto gaatcaacct accgacacca agcaaccatc gatgatgaag ttgtttccat     540
ggagatacta gacactgctg gtcaggaaga taccattcag agggaggggc acatgcgatg     600
gggggaaggc tttgtgctgg tctacgacat tactgaccga ggaagttttg aggaagtgct     660
gccacttaag aacatcctag atgagatcaa aaagcccaag aatgtgactc tcatcttggt     720
tggaaacaaa gctgacttgg accactccag gcaggttagc acagaagaag gagagaagct     780
ggccacagaa ttggcttgtg cttttacga gtgctctgcc tgcactggag aagggaatat     840
cacagagata ttctatgaat tgtgtcgaga ggtgcgtcgc cggaggatgg tgcagggcaa     900
gacgaggcga cgcagctcca ccacgcatgt caagcaagcc attaacaaga tgctcaccaa     960
aatcagtagt taggcagccc agctgaggtg gaccaactaa ttggaaacac tcttcccctt    1020
ctgttcccct ttcaaaaata aaacaaaata ttgcattctt tgtttggatt ctgagaaatg    1080
tctgggcttc ccattgtttc tggcctctaa taggttggga agttttagcg tgttttatgc    1140
aatttcagtg ctaacaattt cttccttttcc tgcttgaata agatacactc taatggcatt    1200
tgaacatgta atcaccagag attctgaaat gactggttta tgttaagcta ttttttaggca    1260
tcttcacctt gctttaagta ggttgaagtt tttgcaaagg catttaaaaa ttcaatttct    1320
tgtcagatac tacaaataat tttcttaaaa gtctaagata gcagaaaata cagtaaaaac    1380
acaggagaag aagctgagct attggaacag gaaatagaag gaactctagt ttctgtttga    1440
agtgaggatt ttctgaatta tctaatatca tctaggtttt cttttaaaatt ttattttgtt    1500
cttcagttca agcatcttct cactaatgtt tttcactata acagaatt catttcaatt    1560
tgagttggtt ctctcaatga tctattgatc attacaccct aactctcctt ccttggctca    1620
aacaatattt tccctataac aaaggcaata ggacacaaaa ttcacatcct gctgggcctt    1680
ttttcatcaa gtcagggtga tataaaaaca ttggaagtct tttcaccaaa ccctgacttt    1740
attgaatgct agtagaagat gtagaattag agacatctga tttgtttatc accttagcag    1800
aaaaaccaca gtccaaaaga caagcaaatt aagaatggag cttaaccatg cctccattgg    1860
gaagtctaga ctttgagcca ggtacagtaa gaaaaattag cctctgattc attaagtttg    1920
ccacatgact tattttgata ttttggatac attaactcac ttaggagaat tcagaaaaga    1980
atgggtgatt aaagttcatt acagctgaat aaatgtgtct aaaacagact cttgtattct    2040
gaaagtacag tctacaactg ataaaacctt atgattcttt tctcccccat tatgcccta     2100
tatatatcaa gatttgggta ctttattta gtagaaaata tatatctttt acatatgtat     2160
```

```
gtatttataa atgcatagat atatgtataa aaatttgtaa gcgttagcgg cattaattca    2220
ccaatgcatt tggacaactt gatgtaactg actttatttt atgtgactat aataaaaagc    2280
ataattttct caaaaaaaaa aaaaaaaa                                        2309
```

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
gtcggtaggt tgattcgagg gtgg                                            24

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
tcatattccc agatgaaccg tttg                                            24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
tctcactaca agagctgact tgcc                                            24

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
ggattctgag aaatgtctgg                                                 20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tcatttcaga atctctggtg                                                 20

<210> SEQ ID NO 9
<211> LENGTH: 217
<212> TYPE: PRT
<213> ORGANISM: Homo sapiens

<400> SEQUENCE: 9

Met Glu Val Glu Asn Glu Ala Ser Cys Ser Pro Gly Ser Ala Ser Gly
 1               5                  10                  15

Gly Ser Arg Glu Tyr Lys Val Val Met Leu Gly Ala Gly Gly Val Gly

-continued

```
                 20                  25                  30
Lys Ser Ala Met Thr Met Gln Phe Ile Ser His Gln Phe Pro Asp Tyr
             35                  40                  45
His Asp Pro Thr Ile Glu Asp Ala Tyr Lys Thr Gln Val Arg Ile Asp
 50                  55                  60
Asn Glu Pro Ala Tyr Leu Asp Ile Leu Asp Thr Ala Gly Gln Ala Glu
 65                  70                  75                  80
Phe Thr Ala Met Arg Glu Gln Tyr Met Arg Gly Glu Gly Phe Ile
                 85                  90                  95
Ile Cys Tyr Ser Val Thr Asp Arg Gln Ser Phe Gln Glu Ala Ala Lys
                100                 105                 110
Phe Lys Glu Leu Ile Phe Gln Val Arg His Thr Tyr Glu Ile Pro Leu
            115                 120                 125
Val Leu Val Gly Asn Lys Ile Asp Leu Glu Gln Phe Arg Gln Val Ser
        130                 135                 140
Thr Glu Glu Gly Leu Ser Leu Ala Gln Glu Tyr Asn Cys Gly Phe Phe
145                 150                 155                 160
Glu Thr Ser Ala Ala Leu Arg Phe Cys Ile Asp Asp Ala Phe His Gly
                165                 170                 175
Leu Val Arg Glu Ile Arg Lys Lys Glu Ser Met Pro Ser Leu Met Glu
            180                 185                 190
Lys Lys Leu Lys Arg Lys Asp Ser Leu Trp Lys Lys Leu Lys Gly Ser
        195                 200                 205
Leu Lys Lys Lys Arg Glu Asn Met Thr
    210                 215

<210> SEQ ID NO 10
<211> LENGTH: 219
<212> TYPE: PRT
<213> ORGANISM: Homo sapiens

<400> SEQUENCE: 10

Met Asp Ser Gly Thr Arg Pro Val Gly Ser Cys Cys Ser Ser Pro Ala
 1               5                  10                  15
Gly Leu Ser Arg Glu Tyr Lys Leu Val Met Leu Gly Ala Gly Gly Val
             20                  25                  30
Gly Lys Ser Ala Met Thr Met Gln Phe Ile Ser His Arg Phe Pro Glu
         35                  40                  45
Asp His Asp Pro Thr Ile Glu Asp Ala Tyr Lys Ile Arg Ile Arg Ile
     50                  55                  60
Asp Asp Glu Pro Ala Asn Leu Asp Ile Leu Asp Thr Ala Gly Gln Ala
 65                  70                  75                  80
Glu Phe Thr Ala Met Arg Asp Gln Tyr Met Arg Ala Gly Glu Gly Phe
                 85                  90                  95
Ile Ile Cys Tyr Ser Ile Thr Asp Arg Arg Ser Phe His Glu Val Arg
                100                 105                 110
Glu Phe Lys Gln Leu Ile Tyr Arg Val Arg Arg Thr Asp Asp Thr Pro
            115                 120                 125
Val Val Leu Val Gly Asn Lys Ser Asp Leu Lys Gln Leu Arg Gln Val
        130                 135                 140
Thr Lys Glu Glu Gly Leu Ala Leu Ala Arg Glu Phe Ser Cys Pro Phe
145                 150                 155                 160
Phe Glu Thr Ser Ala Ala Tyr Arg Tyr Tyr Ile Asp Asp Val Phe His
                165                 170                 175
```

```
Ala Leu Val Arg Glu Ile Arg Arg Lys Glu Lys Glu Ala Val Leu Ala
            180                 185                 190

Met Glu Lys Lys Ser Lys Pro Lys Asn Ser Val Trp Lys Arg Leu Lys
            195                 200                 205

Ser Pro Phe Arg Lys Lys Lys Asp Ser Val Thr
            210                 215
```

<210> SEQ ID NO 11
<211> LENGTH: 156
<212> TYPE: PRT
<213> ORGANISM: Dictyostelium discoideum

<400> SEQUENCE: 11

```
Tyr Asp Pro Thr Ile Glu Asp Ser Tyr Arg Lys Gln Val Ser Ile Asp
 1               5                  10                  15

Asp Glu Thr Cys Leu Leu Asp Ile Leu Asp Thr Ala Gly Gln Glu Glu
            20                  25                  30

Tyr Ser Ala Met Arg Asp Gln Tyr Met Arg Thr Gly Gln Gly Phe Leu
        35                  40                  45

Cys Val Tyr Ser Ile Thr Ser Arg Ser Ser Tyr Asp Glu Ile Ala Ser
 50                  55                  60

Phe Arg Glu Gln Ile Leu Arg Val Lys Asp Lys Asp Arg Val Pro Leu
 65                  70                  75                  80

Ile Leu Val Gly Asn Lys Ala Asp Leu Asp His Glu Arg Gln Val Ser
                85                  90                  95

Val Asn Glu Gly Gln Glu Leu Ala Lys Gly Phe Asn Cys Pro Phe Met
            100                 105                 110

Glu Ser Ser Ala Lys Ser Arg Ile Asn Val Glu Glu Ala Phe Tyr Ser
        115                 120                 125

Leu Val Arg Glu Ile Arg Lys Glu Leu Lys Gly Asp Gln Ser Ser Gly
    130                 135                 140

Lys Ala Gln Lys Lys Lys Lys Gln Cys Leu Ile Leu
145                 150                 155
```

<210> SEQ ID NO 12
<211> LENGTH: 194
<212> TYPE: PRT
<213> ORGANISM: Dictyostelium discoideum

<400> SEQUENCE: 12

```
Met Phe Asn Phe Lys Leu Val Leu Val Gly Pro Gly Gly Val Gly Lys
 1               5                  10                  15

Ser Cys Leu Thr Ile Gln Phe Ile Ala Gln Lys Phe Val Asp Glu Tyr
            20                  25                  30

Asp Pro Thr Leu Glu Asp Ser Tyr Arg Lys Gln Thr Thr Val Asp Gly
        35                  40                  45

Glu Glu Cys Leu Leu Asp Ile Tyr Asp Thr Ala Gly Gln Glu Asp Phe
 50                  55                  60

Ser Ala Val Arg Asp Gln Tyr Met Arg Thr Gly Glu Gly Phe Leu Cys
 65                  70                  75                  80

Val Tyr Ser Ile Thr Tyr Leu Gln Ser Phe Lys Glu Ile His Arg Leu
                85                  90                  95

His Asn His Leu Leu Lys Val Lys Asp Leu Asp Ser Val Pro Phe Val
            100                 105                 110

Leu Val Gly Asn Lys Cys Asp Leu Asn Glu Tyr Arg Glu Val Ser Thr
        115                 120                 125
```

-continued

```
Ala Glu Gly Glu Glu Leu Ala Lys Lys Leu Asn Cys Lys Phe Leu Glu
        130                 135                 140

Thr Ser Ala Lys Glu Arg Ile Asn Val Ser Glu Ser Phe Tyr Glu Leu
145                 150                 155                 160

Val Arg Glu Val Lys Lys Ala Arg Gln Ser Asn Gln His Ser Asn Ser
                165                 170                 175

Gln Glu Gln Asn Thr Asp Gln Pro Ile Lys Lys Lys Ser Cys Asn
        180                 185                 190

Leu Leu
```

<210> SEQ ID NO 13
<211> LENGTH: 183
<212> TYPE: PRT
<213> ORGANISM: Homo sapiens

<400> SEQUENCE: 13

```
Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Ala
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Asn Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Pro Gly Lys Arg Lys
                165                 170                 175

Lys Ser Ser Cys Gln Leu Leu
            180
```

<210> SEQ ID NO 14
<211> LENGTH: 204
<212> TYPE: PRT
<213> ORGANISM: Homo sapiens

<400> SEQUENCE: 14

```
Met Ala Ala Ala Gly Trp Arg Asp Gly Ser Gly Gln Glu Lys Tyr Arg
1               5                   10                  15

Leu Val Val Val Gly Gly Gly Val Gly Lys Ser Ala Leu Thr Ile
            20                  25                  30

Gln Phe Ile Gln Ser Tyr Phe Val Thr Asp Tyr Asp Pro Thr Ile Glu
        35                  40                  45

Asp Ser Tyr Thr Lys Gln Cys Val Ile Asp Asp Arg Ala Ala Arg Leu
    50                  55                  60

Asp Ile Leu Asp Thr Ala Gly Gln Glu Glu Phe Gly Ala Met Arg Glu
```

-continued

```
                65                  70                  75                  80
Gln Tyr Met Arg Thr Gly Glu Gly Phe Leu Val Phe Ser Val Thr
                        85                  90                  95

Asp Arg Gly Ser Phe Glu Glu Ile Tyr Lys Phe Gln Arg Gln Ile Leu
                    100                 105                 110

Arg Val Lys Asp Arg Asp Glu Phe Pro Met Ile Leu Ile Gly Asn Lys
                    115                 120                 125

Ala Asp Leu Asp His Gln Arg Gln Val Thr Gln Glu Glu Gly Gln Gln
            130                 135                 140

Leu Ala Arg Gln Leu Lys Val Thr Tyr Met Glu Ala Ser Ala Lys Ile
145                 150                 155                 160

Arg Met Asn Val Asp Gln Ala Phe His Glu Leu Val Arg Val Ile Arg
                    165                 170                 175

Lys Phe Gln Glu Gln Glu Cys Pro Pro Ser Pro Glu Pro Thr Arg Lys
                    180                 185                 190

Glu Lys Asp Lys Lys Gly Cys His Cys Val Ile Phe
                    195                 200
```

<210> SEQ ID NO 15
<211> LENGTH: 206
<212> TYPE: PRT
<213> ORGANISM: Homo sapiens

<400> SEQUENCE: 15

```
Met Ala Ala Asn Lys Pro Lys Gly Gln Asn Ser Leu Ala Leu His Lys
1               5                   10                  15

Val Ile Met Val Gly Ser Gly Gly Val Gly Lys Ser Ala Leu Thr Leu
                20                  25                  30

Gln Phe Met Tyr Asp Glu Phe Val Glu Asp Tyr Glu Pro Thr Lys Ala
            35                  40                  45

Asp Ser Tyr Arg Lys Lys Val Val Leu Asp Gly Glu Glu Val Gln Ile
        50                  55                  60

Asp Ile Leu Asp Thr Ala Gly Gln Glu Asp Tyr Ala Ala Ile Arg Asp
65                  70                  75                  80

Asn Tyr Phe Arg Ser Gly Glu Gly Phe Leu Cys Val Phe Ser Ile Thr
                    85                  90                  95

Glu Met Glu Ser Phe Ala Ala Thr Ala Asp Phe Arg Glu Gln Ile Leu
                    100                 105                 110

Arg Val Lys Glu Asp Glu Asn Val Pro Phe Leu Leu Val Gly Asn Lys
                    115                 120                 125

Ser Asp Leu Glu Asp Lys Arg Gln Val Ser Val Glu Glu Ala Lys Asn
            130                 135                 140

Arg Ala Glu Gln Trp Asn Val Asn Tyr Val Glu Thr Ser Ala Lys Thr
145                 150                 155                 160

Arg Ala Asn Val Asp Lys Val Phe Phe Asp Leu Met Arg Glu Ile Arg
                    165                 170                 175

Ala Arg Lys Met Glu Asp Ser Lys Glu Lys Asn Gly Lys Lys Lys Arg
                    180                 185                 190

Lys Ser Leu Ala Lys Arg Ile Arg Glu Arg Cys Cys Ile Leu
                    195                 200                 205
```

<210> SEQ ID NO 16
<211> LENGTH: 60
<212> TYPE: PRT
<213> ORGANISM: consensus

```
<400> SEQUENCE: 16

Lys Gly Gly Gly Val Gly Lys Ser Ala Thr Gln Phe Phe Asp Pro Thr
 1               5                  10                  15

Glu Asp Tyr Asp Ile Leu Asp Thr Ala Gly Gln Ala Arg Tyr Met Arg
            20                  25                  30

Gly Gly Phe Ser Thr Ser Phe Val Pro Leu Val Gly Asn Lys Asp Leu
        35                  40                  45

Arg Val Glu Gly Leu Ala Glu Ser Ala Phe Leu Arg
 50                  55                  60
```